US011980556B2

(12) United States Patent
Sanati et al.

(10) Patent No.: US 11,980,556 B2
(45) Date of Patent: *May 14, 2024

(54) BALLOON CATHETERS AND METHODS FOR USE

(71) Applicant: Ostial Corporation, Campbell, CA (US)

(72) Inventors: Archimedes Sanati, Campbell, CA (US); Farhad Khosravi, Los Altos Hills, CA (US)

(73) Assignee: Ostial Corporation, Campbell, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 17/234,662

(22) Filed: Apr. 19, 2021

(65) Prior Publication Data
US 2021/0236312 A1    Aug. 5, 2021

Related U.S. Application Data

(63) Continuation of application No. 16/017,627, filed on Jun. 25, 2018, now Pat. No. 10,980,652, which is a (Continued)

(51) Int. Cl.
*A61F 2/954*    (2013.01)
*A61F 2/30*    (2006.01)
(Continued)

(52) U.S. Cl.
CPC .............. *A61F 2/954* (2013.01); *A61F 2/958* (2013.01); *A61F 2002/30322* (2013.01);
(Continued)

(58) Field of Classification Search
CPC .. A61F 2/95; A61F 2/954; A61F 2/958; A61F 2002/30322; A61F 2002/821;
(Continued)

(56) References Cited

U.S. PATENT DOCUMENTS

4,878,495 A * 11/1989 Grayzel ............. A61M 25/1011
606/193
9,034,025 B2 * 5/2015 Sanati ..................... A61F 2/954
623/1.11
(Continued)

*Primary Examiner* — Mohamed G Gabr
(74) *Attorney, Agent, or Firm* — William A. English; Vista IP Law Group LLP (57) ABSTRACT

Apparatus and methods are provided for flaring a stent deployed within a branch vessel including an ostium communicating with a main vessel, a first end of the stent extending at least partially from the branch. A catheter is provided that includes a first balloon carried on its distal end, and a second balloon that includes a distal section overlying at least a portion of the first balloon and a proximal section. The catheter distal end is introduced into the main vessel and positioned through the ostium and stent into the branch until the first balloon is disposed within the stent. The first balloon is expanded to anchor the stent, and the second balloon is expanded to flare the first end of the stent. Optionally, the first balloon is expanded further, e.g., to expand the stent within the branch body lumen and/or dilate the lesion.

19 Claims, 5 Drawing Sheets

Related U.S. Application Data continuation of application No. 14/715,279, filed on May 18, 2015, now Pat. No. 10,004,622, which is a continuation of application No. 13/602,074, filed on Aug. 31, 2012, now Pat. No. 9,034,025, and a continuation-in-part of application No. 11/466,439, filed on Aug. 22, 2006, now Pat. No. 10,092,429, and a continuation-in-part of application No. 12/983,860, filed on Jan. 3, 2011, now abandoned, which is a continuation of application No. 11/136,266, filed on May 23, 2005, now Pat. No. 7,862,601.

(60) Provisional application No. 61/529,890, filed on Aug. 31, 2011.

(51) Int. Cl.
| | | |
|---|---|---|
| *A61F 2/82* | (2013.01) | |
| *A61F 2/95* | (2013.01) | |
| *A61F 2/958* | (2013.01) | |
| *A61M 25/10* | (2013.01) | |

(52) U.S. Cl.
CPC ............ *A61F 2002/821* (2013.01); *A61F 2/95* (2013.01); *A61F 2230/0071* (2013.01); *A61F 2250/0018* (2013.01); *A61F 2250/0026* (2013.01); *A61F 2250/0039* (2013.01); *A61M 25/1002* (2013.01); *A61M 25/1011* (2013.01)

(58) Field of Classification Search
CPC ...... A61F 2230/0071; A61F 2250/0018; A61F 2250/0026; A61F 2250/0039; A61M 25/1002; A61M 25/1011
See application file for complete search history.

(56) References Cited

U.S. PATENT DOCUMENTS

| | | | | |
|---|---|---|---|---|
| 10,004,622 | B2* | 6/2018 | Sanati | ............... A61F 2/954 |
| 10,980,652 | B2* | 4/2021 | Sanati | ............... A61F 2/958 |
| 11,510,797 | B2* | 11/2022 | Yang | ............... A61M 25/10 |

* cited by examiner

BALLOON CATHETERS AND METHODS FOR USE

This application is a continuation of co-pending application Ser. No. 16/017,627, filed Jun. 25, 2018, issuing as U.S. Pat. No. 10,980,652, which is a continuation of application Ser. No. 14/715,279, filed May 18, 2015, now U.S. Pat. No. 10,004,622, which is a continuation of application Ser. No. 13/602,074, filed Aug. 31, 2012, now U.S. Pat. No. 9,034,025, which claims benefit of provisional application Ser. No. 61/529,890, filed Aug. 31, 2012, and is a continuation-in-part of application Ser. No. 11/466,439, filed Aug. 22, 2006, now U.S. Pat. No. 10,092,429, and Ser. No. 12/983,860, filed Jan. 3, 2011, abandoned, which is a continuation of Ser. No. 11/136,266, filed May 23, 2005, now U.S. Pat. No. 7,862,601.

The entire disclosures of these applications are expressly incorporated by reference herein.

FIELD OF THE INVENTION

The present invention relates generally to apparatus and methods for treating stenoses, occlusions, or other lesions within a body lumen, such as an artery or other blood vessel, and, more particularly, to apparatus and methods for flaring or otherwise expanding stents deployed within a body lumen, such as a branch vessel including an ostium extending from a main vessel or trunk.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location. Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

Vascular stenoses, e.g., within arteries supplying the heart, can lead to hypoflow conditions in the vessel, which may cause ischemia and/or infarction of the organ being supplied by that vessel, e.g., the heart. Sometimes, a stenosis or other lesion may occur at an ostium or bifurcation, i.e., where a branch vessel extends from a main vessel or trunk. In such situations, it may be difficult to visualize the lesion and/or accurately position a stent within the ostium and/or branch vessel.

Often, when the stent is deployed in such anatomy, one end of the stent may extend out from the ostium into the main vessel, e.g., into the aorta from a coronary artery, common carotid artery, or peripheral artery. Such a position of the stent may cause difficulty in future endoluminal interventions, e.g., reentering the branch vessel, which may require recrossing the stent. In addition, there may be risk that the end of the stent extending from the ostium may cause damage to neighboring structures, such as aortic valve leaflets adjacent to the ostium of a coronary vessel.

To address these problems, it has been suggested to over-expand or flare the end of the stent extending into the main vessel, e.g., to direct the end of the stent against or closer to the wall of the ostium. Thereafter, it may be easier to recross the stent in case future endovascular study or intervention is required. In addition, in the case of coronary stents, flaring the end of the stent extending into the aorta may also move the end further from the aortic lumen and decrease the risk of damage to the aortic leaflets.

Accordingly, apparatus and methods for flaring and/or otherwise expanding stents would be useful.

SUMMARY OF THE INVENTION

The present invention is directed to apparatus and methods for treating stenoses, occlusions, or other lesions within a body lumen, such as an artery or other blood vessel. More particularly, the present invention is directed to apparatus and methods for flaring and/or otherwise expanding stents deployed within a body lumen, such as a branch vessel including an ostium extending from another main vessel or trunk.

In accordance with one embodiment, a method is provided for flaring a stent deployed within a branch body lumen including an ostium communicating with a main body lumen, a first end of the stent extending at least partially from the branch body lumen into the ostium and/or main body lumen. To accomplish this, a catheter or other elongate member may be used that includes a proximal end, a distal end, a first balloon carried on the distal end that includes a main section when expanded, and a second balloon carried on the distal end that includes a distal section overlying at least a portion of the main section of the first balloon and a proximal section extending proximally from the distal section and/or the first balloon.

The distal end of the elongate member may be introduced into the main body lumen, e.g., with the first and second balloons in contracted conditions. The distal end of the elongate member may be positioned through the ostium and stent into the branch body lumen until the main section is disposed within the stent and/or distally beyond the stent, e.g., using external imaging and markers on the distal end to facilitate positioning the proximal section of the second balloon adjacent the ostium.

The first balloon may be expanded to substantially anchor the stent relative to the branch body lumen, and the proximal section of the second balloon may be expanded to flare the first end of the stent within the ostium. Optionally, after expanding the proximal section of the second balloon, the first balloon may be expanded further, e.g., to expand the stent within the branch body lumen and/or dilate the lesion.

In accordance with another embodiment, a method is provided for treating a lesion within a branch body lumen including an ostium communicating with a main body lumen that includes introducing a distal end of a delivery catheter into the main body lumen, the delivery catheter distal end carrying a stent in a contracted condition; positioning the delivery catheter distal end within the branch body lumen such that a first end of the stent is disposed adjacent the ostium and a second end of the stent is disposed further within the branch body lumen; and expanding the stent to a substantially uniform diameter such that the stent engages surrounding tissue of the branch body lumen.

Thereafter, the first end of the stent may be flared, e.g., using a flaring catheter including a proximal end, a distal end, a first balloon carried on the flaring catheter distal end that includes a main section when expanded, and a second balloon carried on the flaring catheter distal end that includes a distal section overlying at least a portion of the main section of the first balloon and a proximal section extending proximally from the distal section and/or the first balloon. The flaring catheter distal end may be introduced into the main body lumen, and positioned through the ostium and stent into the branch body lumen until the main section is disposed within the stent.

The first balloon may be expanded to substantially anchor the stent relative to the branch body lumen, and the proximal section of the second balloon may be expanded to flare the first end of the stent within the ostium. Optionally, after expanding the proximal section of the second balloon, the first balloon may be expanded further, e.g., to expand the stent within the branch body lumen and/or dilate the lesion. In addition or alternatively, the lesion may be dilated when the stent is expanded, e.g., to a substantially uniform diameter by the main section of the first balloon.

In accordance with still another embodiment, a method is provided for expanding a stent previously deployed within a body lumen using an elongate member including a proximal end, a distal end, a first balloon carried on the distal end that includes a substantially uniform diameter main section when expanded, and a second balloon carried on the distal end that includes a distal section overlying at least a portion of the uniform diameter section of the first balloon and a proximal section extending proximally from the distal section and the first balloon. The distal end of the elongate member may be positioned within the body lumen until the main section is disposed within the stent, and the proximal section of the second balloon may be expanded to substantially anchor the elongate member distal end, and consequently, the first balloon, relative to the stent. The main section of the first balloon may then be expanded to expand the stent and/or dilate a lesion surrounding the stent, the second balloon preventing axial migration of the distal end.

In accordance with yet another embodiment, a method is provided for treating a stenosis within a body lumen using an elongate member including a proximal end, a distal end, a first balloon carried on the distal end that includes a substantially uniform diameter main section when expanded, and a second balloon carried on the distal end that includes a distal section overlying at least a portion of the uniform diameter section of the first balloon and a proximal section extending proximally from the distal section and the first balloon. The distal end of the elongate member may be positioned within the body lumen until the main section is disposed within the stenosis, and the proximal section of the second balloon may be expanded to substantially anchor the elongate member distal end relative to the stenosis. The main section of the first balloon may then be expanded to dilate the stenosis, the second balloon preventing axial migration of the distal end.

In accordance with still another embodiment, a method is provided for treating a stenosis within a body lumen using an elongate member including a proximal end, a distal end, a first balloon carried on the distal end that includes a substantially uniform diameter main section when expanded, and a second balloon carried on the distal end adjacent the main section of the first balloon, e.g., proximal or distal to the main section. The distal end of the elongate member may be positioned within the body lumen until the main section is disposed within the stenosis, e.g., such that the second balloon is positioned adjacent, i.e., proximal or distal to, the stenosis. The second balloon may then be expanded to substantially anchor the elongate member distal end relative to the stenosis. The main section of the first balloon may then be expanded to dilate the stenosis, the second balloon preventing axial migration of the distal end.

In accordance with yet another embodiment, a method is provided for treating a region within a body lumen using an elongate member including a proximal end, a distal end, a first balloon carried on the distal end that includes a substantially uniform diameter main section when expanded, and a second balloon carried on the distal end that includes a first section overlying at least a portion of the uniform diameter section of the first balloon and a second section disposed adjacent the main section of the first balloon. The distal end of the elongate member may be positioned within the body lumen until the main section is disposed within a treatment region, and the second section of the second balloon may be expanded to substantially anchor the elongate member distal end relative to the treatment region. The main section of the first balloon may then be expanded to contact and treat the treatment region, the second balloon preventing axial migration of the elongate member distal end.

In one embodiment, the second section of the second balloon extends proximally from the main section of the first balloon. In another embodiment, the second section of the second balloon extends distally from the main section of the first balloon. In yet another embodiment, a second section may be provided proximal to the main section and a third section may be provided distal to the main section, e.g., such that the second balloon expands both proximally and distally to the main section of the first balloon, e.g., substantially simultaneously. In addition or alternatively, the first section of the second balloon may extend entirely over the main section of the first balloon or may extend only partially over the main section.

In an exemplary embodiment, the treatment region may be a stenosis within a blood vessel, e.g., within a branch vessel adjacent an ostium communicating with a main vessel. In another embodiment, the treatment region may be the site of a natural or prosthetic valve, e.g., the site of an aortic valve.

In accordance with still another embodiment, a method is provided for treating a valve within a body lumen of a patient using an elongate member including a proximal end, a distal end, a first balloon carried on the distal end that includes a substantially uniform diameter main section when expanded, and a second balloon carried on the distal end that includes a first section overlying at least a portion of the uniform diameter section of the first balloon and a second section adjacent the main section of the first balloon. The distal end of the elongate member is positioned within the body lumen with the first and second balloons collapsed until the main section is disposed within a valve. The second section of the second balloon is expanded to substantially anchor the distal end relative to the valve, and then the main section of the first balloon is expanded to dilate leaflets of the valve.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1A:
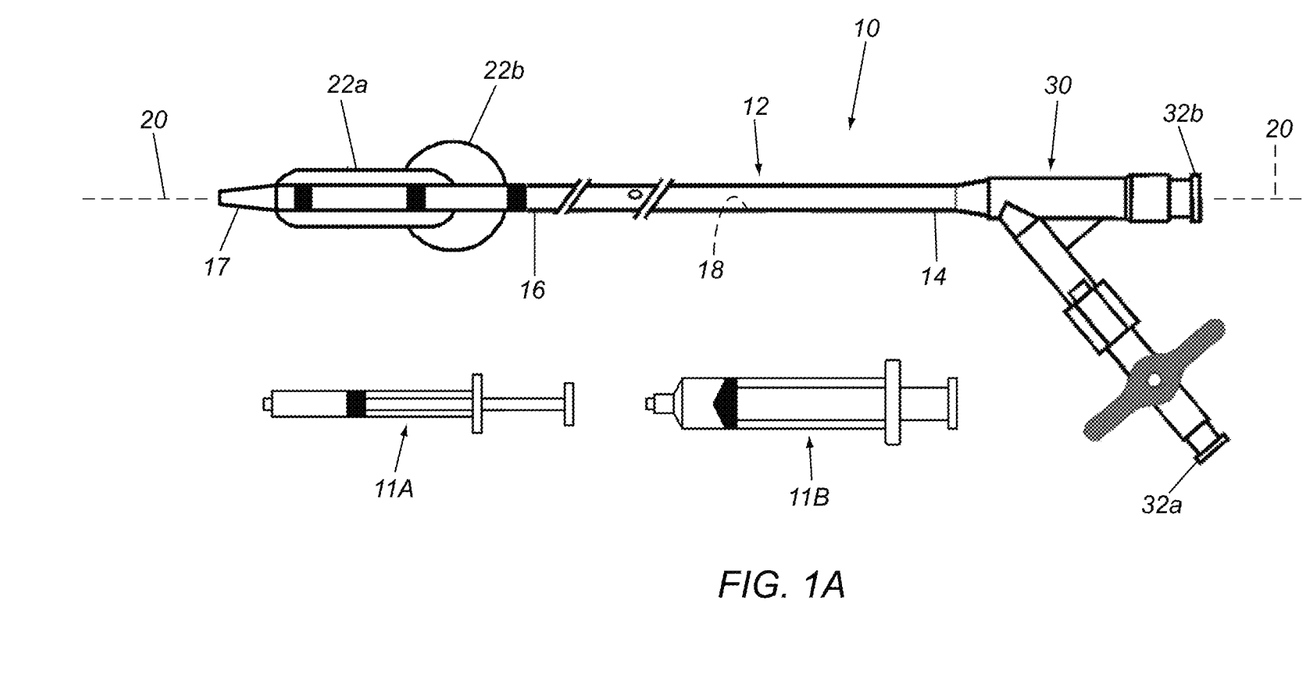
FIG. 1A is a side view of an exemplary embodiment of a catheter including overlapping balloons for flaring and/or otherwise expanding a stent previously deployed within a body lumen.
Figure 1B:
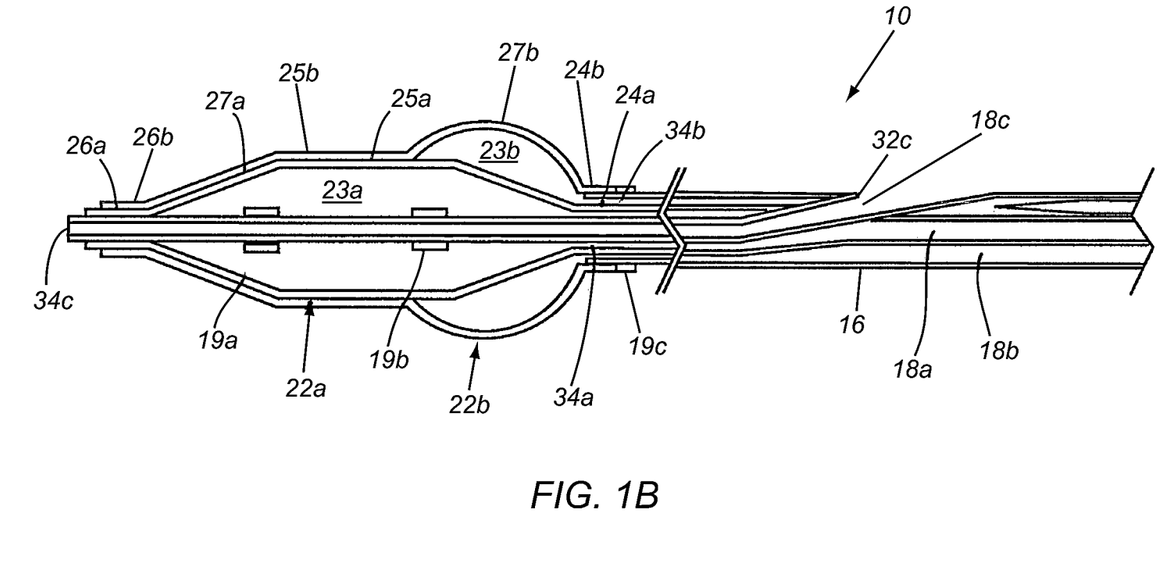
FIG. 1B is a cross-sectional detail of a distal end of the catheter of FIG. 1A with the balloons expanded.

Turning to the drawings, FIGS. 1A and 1B show an exemplary embodiment of an apparatus 10 for flaring and/or otherwise expanding a stent or other prosthesis (not shown), e.g., within or adjacent an ostium or other bifurcation between a main lumen and a branch lumen (also not shown). Generally, the apparatus 10 includes a catheter or other elongate tubular member 12 having a proximal end 14, a distal end 16, and one or more lumens 18 extending between the proximal and distal ends 14, 16, thereby defining a longitudinal axis 20 extending between the proximal and distal ends 14, 16.

As shown, the catheter 12 may include a pair of overlapping balloons or other expandable members 22 on the distal end 16, e.g., for flaring and/or otherwise expanding a stent previously deployed within a body lumen (not shown), as described further below. In addition, the distal end 16 may include one or more markers, e.g., one or more bands of radiopaque material 19, to facilitate positioning the catheter 12 relative to a stent and/or anatomical structures within a patient's body. In addition or alternatively, the catheter 12 may include one or more therapeutic and/or diagnostic elements (not shown) on the distal end 16, e.g., within or carried by the balloon(s) 22, as described further below.

Optionally, the apparatus 10 may be provided as a kit or system including one or more additional components, such as syringes 11, a guide catheter, and/or one or more guidewires (not shown).

The catheter 12 may be formed from one or more tubular bodies, e.g., having variable flexibility along its length. For example, the distal end 16 may be substantially flexible to facilitate introduction through tortuous anatomy, e.g., terminating in a rounded, tapered, and/or other substantially atraumatic distal tip 17. The distal end 16 may be sized and/or shaped for introduction into a body lumen, e.g., having a diameter between about one and seven millimeters (1-7 mm), or less than 1.7 millimeters. The proximal end 14 may be substantially flexible, semi-rigid, or rigid, e.g., having sufficient column strength to facilitate advancing the distal end 16 through a patient's vasculature by pushing on the proximal end 14. Optionally, a shaft support wire or other stiffener (not shown) may be provided within the proximal end 14, if desired, e.g., to facilitate pushing the catheter 12 from the proximal end 14. The catheter 12 may be formed from plastic, metal, or composite materials, e.g., a plastic material having a wire, braid, or coil core, which may prevent kinking or buckling of the catheter 12 during advancement.

As shown in FIG. 1A, the catheter 12 may include a handle 30 on the proximal end 14, e.g., to facilitate manipulating the catheter 12. The handle 30 may include one or more ports 32 communicating with respective lumens 18 within the catheter 12, as described further below. The handle 30 may be molded, machined, or otherwise formed from plastic, metal, or composite material, e.g., providing an outer casing, which may be contoured or otherwise shaped to ease manipulation. The proximal end 14 of the catheter 12 may be attached to the handle 30, e.g., by bonding, cooperating connectors, interference fit, and the like. Optionally, if the apparatus 10 includes any actuatable components (not shown) on the distal end 16, the handle 30 may include one or more actuators (also not shown), such as one or more slides, dials, buttons, and the like, for actuating or otherwise manipulating the components from the proximal end 14.

In the exemplary embodiment shown in FIG. 1B, the catheter 12 includes at least three lumens 18 extending between the proximal and distal ends 14, 16. For example, the catheter 12 may include inflation lumens 18a, 18b that extend from ports 32a, 32b in the handle 30 through the catheter 12 to openings 34a, 34b and communicate within interiors 23a, 23b of respective balloons 22a, 22b. The ports 32a, 32b on the handle 30 may include connectors, e.g., a luer lock connector (not shown), one or more seals (also not shown), and the like. A source of inflation media and/or vacuum, e.g., one of the syringes 11 filled with saline or other inflation media, may be connected to the ports 32a, 32b, e.g., directly or via tubing (also not shown), for expanding and/or collapsing the balloons 22a, 22b.

In addition, the catheter 12 may include an instrument lumen 18c that extends from port 32c to an opening 34c in the distal tip 17. The instrument lumen 18c may have sufficient size to allow a guidewire or other rail or instrument (not shown) to be inserted therethrough, e.g., to facilitate advancing the catheter 12 over the rail, as explained further below. Alternatively, rather than a "rapid exchange" instrument lumen 18c, an instrument lumen (not shown) may be provided that extends from the handle 30 to the distal end 16. In this alternative, the handle 30 may include a port (not shown) and/or one or more seals (also not shown) that prevent fluid, e.g., blood, from flowing proximally out of the port, yet allow one or more instruments to be inserted therethrough and into the instrument lumen 18c.

As shown in FIG. 1B, the lumens 18 are disposed adjacent one another. Alternatively, the lumens 18 may be disposed in concentric or other arrangements within the body of the catheter 12. In addition, if the apparatus 10 includes additional balloons (not shown) on the distal end 16, the catheter 12 may include one or more additional inflation lumens (also not shown), and the handle 30 may include one or more additional ports (also not shown).

Alternatively, other configurations of lumens may be provided for delivering fluid to and/or aspirating fluid from one or both balloons 22. For example, a single lumen may be provided (not shown) that communicates with the interiors 23 of both balloons 22. This embodiment may allow the balloons 22 to be expanded and/or collapsed substantially simultaneously using a single syringe or other source of fluid/vacuum. In another alternative, the catheter 12 may include separate inflation lumens 18a, 18b, but the handle 30 may include a single side port (not shown) to which a syringe or other source of fluid/vacuum may be connected. In this alternative, the handle 30 may include a switch, stopcock, valve, or other device (not shown) for selectively connecting one or both inflation lumens 18a, 18b to the side port, similar to embodiments in the applications incorporated by reference herein.

Returning to FIGS. 1A and 1B, the catheter 12 includes a first or inner balloon 22a and a second or outer balloon 22b on the distal end 16, which are expandable independently of one another. The balloons 22 may be bonded or otherwise secured to the distal end 16 of the catheter 12, e.g., by bonding with adhesive, sonic welding, using an annular collar or sleeve, and the like. For example, as best seen in FIG. 1B, the inner balloon 22a may include a proximal end 24a attached directly to the distal end 16 of the catheter 12 distal to instrument lumen port 32c and a distal end 26a attached directly to the distal end 16 adjacent the distal tip 17.

The outer balloon 22b includes a first or distal section 25b that extends at least partially over the inner balloon 22a and a second or proximal section 27b. For example, the first section 25b may extend entirely over the inner balloon 22a and a distal end 26b of the outer balloon 22b may be attached over or adjacent to the distal end 26a of the inner balloon 22a, e.g., by bonding, sonic welding, and the like, as described elsewhere herein. A proximal end 24b of the outer balloon 22b may be attached to the distal end 16 of the catheter 12, e.g., proximal or adjacent to the inner balloon proximal end 24a and distal to the instrument lumen port 32c.

The first section 25b of the outer balloon 22b may overlie but remain separate from the underlying inner balloon 22a. Alternatively, the first section 25b may be bonded or otherwise attached to the inner balloon 22a, e.g., continuously or intermittently along the inner balloon 22a. Alternatively, the orientation of the outer balloon 22b may be reversed, if desired, e.g., with the second section 25b of the outer balloon 22b extending distally relative to the main section 25a of the inner balloon 22a rather than proximally. In a further alternative, a substantially spherical or bulbous section may be provided on the outer balloon 22b both proximally and distally to the main section 25a of the inner balloon 22a (not shown). In this alternative, the proximal and distal sections may be expanded simultaneously or independently of one another, as desired.

The inner balloon 22a may be expandable from a contracted condition (not shown) to an enlarged condition (shown in FIGS. 1A and 1B). Similarly, the outer balloon 22b may also be expandable from a contracted condition (not shown) to an enlarged condition (shown in FIGS. 1A and 1B). One or both balloons 22, e.g., inner balloon 22a, may be formed from substantially inelastic material, e.g., PET, nylon, or PEBAX, such that the balloon 22 expands to a predetermined size in its enlarged condition once sufficient fluid is introduced into the interior of the balloon 622. In addition or alternatively, one or both balloons 22, e.g., outer balloon 22b, may be formed from substantially elastic material, e.g., silicone, polyurethane, or polyethylene, such that the balloon 22 may be expanded to a variety of sizes depending upon the volume and/or pressure of fluid within the interior. In an exemplary embodiment, the inner balloon 22a may be formed from a semi-compliant or substantially non-compliant material, e.g., mid to high durometer PEBAX, nylon, or PET, and the outer balloon 22b may be formed from a substantially complaint or semi-compliant material, e.g., polyethylene, polyurethane, and low to mid durometer PEBAX.

To provide the proximal and distal sections 27b, 25b of the outer balloon 22b, the balloon material may be formed into a shape including a substantially spherical or other bulbous shape for the proximal section 27b and a substantially uniform, smaller diameter shape for the distal section 25b. For example, the balloon material may be blow molded within a mold having the desired shape for the outer balloon 22b when inflated. Because of the compliance of the balloon material, the outer balloon 22b, e.g., the proximal section 27b, may be expanded greater than the relaxed molded shape, yet may substantially maintain that shape unless constrained by external forces.

The outer balloon 22b may have a substantially uniform wall thickness, e.g., between the proximal and distal sections 27b, 25b. Alternatively, the wall thickness may vary; for example, the proximal section 27b may have a thinner wall thickness than the distal section 25b. Optionally, the outer balloon 22b may include one or more features thereon for enhancing traction, friction, or other engagement with structure contacted by the outer balloon 22b when expanded. For example, the outer surface of at least the proximal section 27b may be treated or textured, may include ribs or other protrusions, and the like (not shown) to increase friction or other engagement upon expansion.

In addition or alternatively, the balloons 22 may operate under different internal pressures and/or may require different pressures sufficient to fully expand the respective balloons 22. For example, the inner balloon 22a may require a greater inflation pressure to fully expand than the outer balloon 22b. This may allow the proximal section 27b of the outer balloon 22b to be expanded using a lower inflation pressure to flare and/or shape a flaring portion of a stent without substantial expansion of a main portion of the stent, as described further elsewhere herein and in the applications incorporated by reference herein.

Alternatively, during use, the outer balloon 22b may be inflated based upon delivering one or more predetermined volumes of fluid therein, e.g., in multiple stages of expansion, as described further below. For example, the proximal section 27b of the outer balloon 122a may be inflated upon delivering a first predetermined volume of fluid therein to flare the stent, e.g., between about 0.25-2 cubic centimeters or between about 0.5-4.2 cubic centimeters. Volume-based delivery may be useful for describing the function of the outer balloon 22b because of its relative compliance and/or low pressure requirements, as explained in the applications incorporated by reference herein.

As shown in FIGS. 1A and 1B, the proximal section 27b of the outer balloon 22b may be shaped to expand to a substantially spherical shape in the enlarged condition, e.g., having a diameter between about ten and twenty millimeters (10-20 mm) when expanded using an inflation pressure between about one and five atmospheres (1-5 ATM). In an exemplary embodiment, the proximal section 27b of the outer balloon 22b may have a diameter of about thirteen millimeters (13 mm) at an inflation pressure of about two atmospheres (2 ATM). In contrast, the inner balloon 122b may be shaped to expand to a substantially cylindrical shape in the enlarged condition, e.g., having a diameter between about two and eight millimeters (2-8 mm) when expanded using an inflation pressure between about eight and twenty atmospheres (8-20 ATM).

In addition, a main section 25a of the inner balloon 22a may have a substantially uniform diameter, e.g., having a length between about eight and thirty millimeters (8-30 mm). Beyond the uniform diameter portion, the inner balloon 22a may have a transition portion 27a adjacent the distal tip 17. The transition portion 27a may be tapered, as shown, or may be substantially blunt, i.e., extending inwardly to the distal tip 17 (not shown). As shown, the main portion 25a of the inner balloon 22a may underlie at least a portion of the outer balloon 22b, e.g., the distal section 25b, as shown in FIG. 1B and as disclosed in the applications incorporated by reference elsewhere herein. In an exemplary embodiment, the main section 27a of the inner balloon 22a may have a diameter of between about five and six millimeters (5-6 mm) in the enlarged condition and may have a length of at least about seventeen millimeters (17 mm) distally beyond the proximal section 27b of the outer balloon 22b.

Optionally, the balloons 22 may include one or more diagnostic and/or therapeutic elements. For example, in one embodiment, the outer balloon 22b may carry one or more therapeutic agents, e.g., at or adjacent the transition zone between the proximal and distal sections 27b, 25b. The therapeutic agent(s) may be pressed against the wall of a vessel, e.g., at an ostium, lesion, or within a branch, as described further below.

In another embodiment, one or more electrodes or other elements (not shown) may be provided on the balloons for delivering energy to tissue contacted by the balloons 22. For example, one or more electrodes may be provided on the outer balloon 22b, e.g., at or adjacent the transition zone between the proximal and distal sections 27b, 25b. Alternatively, one or more ultrasound elements may be provided on the distal end 16, e.g., on an inner surface of the outer balloon 22b, on the inner balloon 22a, and/or on the distal end 16 itself within the balloons 22. In this alternative, the inflation media used to expand the balloons 22 may be selected that easily transmits ultrasonic energy to facilitate application of ultrasound to tissue surrounding the balloons 22. In these options, the handle 30 may include one or more actuators (not shown) for selectively activating and deactivating the energy element(s) on the distal end 16. In addition or alternatively, one or more connectors (also not shown) may be provided on the handle 30 for coupling the energy element(s) to a driver, controller, or other source of electrical, ultrasound, or other energy (not shown).

Turning to FIGS. 2A-2F, an exemplary method is shown for using the apparatus 10 to flare and/or otherwise expand a stent 40 deployed within a patient's body, e.g., including an ostium 90. As shown, the ostium 90 may be an opening in a wall of a first or main body lumen or trunk 92 that communicates with a second body lumen or branch 94. In exemplary embodiments, the main body lumen 92 may be the ascending or descending aorta, and the branch body lumen may be a coronary artery, a common carotid artery, or a peripheral artery. A stenosis, occlusion, or other lesion 96 may exist at and/or adjacent to the ostium 90, e.g., extending at least partially into the branch 94. The lesion 96 may include atherosclerotic plaque or other material that partially or completely occludes blood or other fluid flow between the trunk 92 and the branch 94.

Figure 2A:
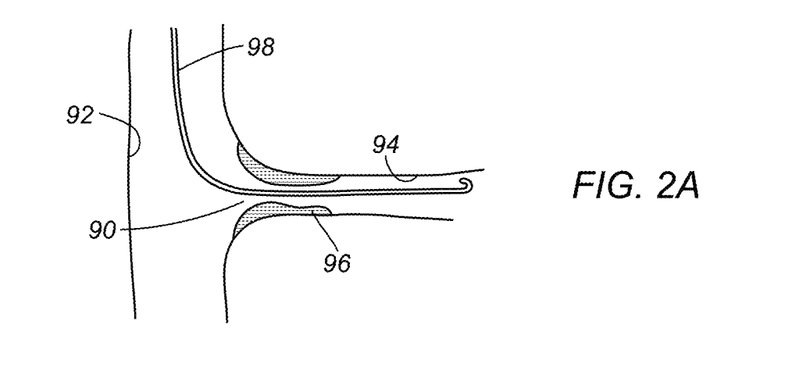
FIGS. 2A-2F are cross-sectional views of a patient's body including an ostium communicating between a main vessel and a branch vessel, showing a method for flaring a stent previously deployed within the branch vessel using the apparatus of FIGS. 1A and 1B.

Initially, as shown in FIG. 2A, a guidewire 98 or other rail may be introduced from the trunk 92 through the ostium 90 into the branch 94, e.g., using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of a guide catheter (not shown). For example, a distal end of a guide catheter (not shown) may be advanced over the guidewire 98 into the trunk 92, e.g., until the distal end is disposed adjacent or proximal to the ostium 90. The guide catheter may be used to advance one or more instruments (such as any of the catheters or other devices described herein) over the guidewire 98 and into the trunk 92 and/or branch 94.

If the lesion 96 completely occludes the branch 94, the guidewire 98 may be directed through the occlusion, or other devices (not shown) may be advanced over the guidewire 98 or otherwise in conjunction with the guidewire 98 to create a passage through the lesion 96 for the guidewire 98.

After the guidewire 98 is directed into the branch 94 beyond the lesion 96, it may be desirable to at least partially dilate the lesion 96. For example, an angioplasty catheter (not shown) may be advanced through the guide catheter and/or over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 40 is implanted. After completing any such procedures, any instruments advanced over the guidewire 98 may be removed.

Figure 2B:
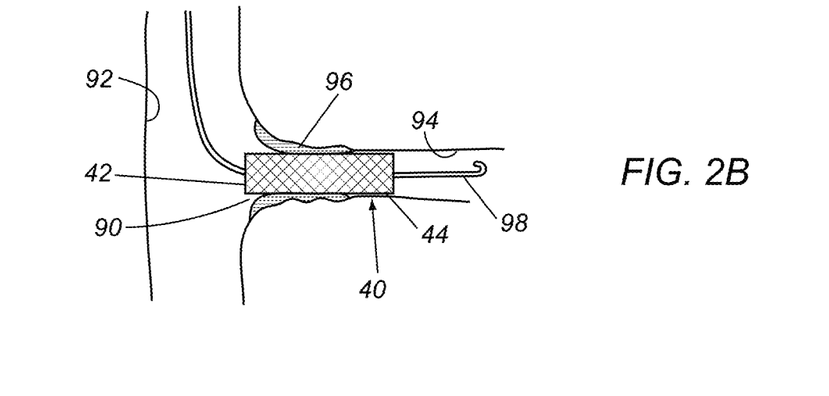

To deliver the stent 40, any delivery catheter and/or conventional procedure may be used. For example, a distal end of a delivery catheter (not shown) may be advanced over the guidewire 98 and/or through the guide catheter from the entry site into the trunk 92. For example, with the distal end of the guide catheter against or adjacent the ostium 90, the distal end of the delivery catheter may be advanced from the guide catheter, through the ostium 90, and into the branch 94. The delivery catheter may be positioned such that the stent 40 extends into and through the lesion 96 and/or branch 94. The stent 40 may be expanded and/or otherwise deployed from the delivery catheter to place the stent 40 across the lesion 96 and/or within the branch 94. For example, as shown in FIG. 2B, the stent 40 may be deployed such that a first end 42 of the stent 40 extends at least partially into the ostium 90 and/or the trunk 92, and a second end 44 of the stent 40 is disposed within the branch 94 beyond the lesion 96.

As shown, the stent 40 may have a substantially uniform diameter cross-section once deployed. For example, the stent 40 may be expanded to dilate and/or otherwise engage the lesion 96 and/or branch 94. Alternatively, the stent 40 may be partially expanded using the delivery catheter, allowing the stent 40 to be further expanded by the apparatus 10, as described below.

Figure 2C:
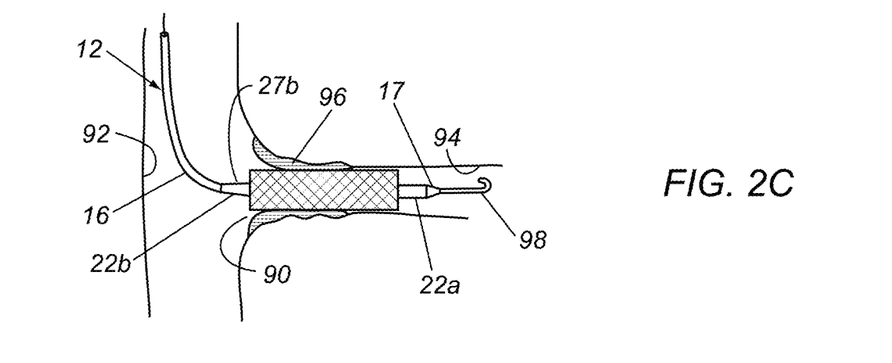

Turning to FIG. 2C, thereafter, the distal end 16 of the flaring catheter 12 (with the balloons 22 in their contracted conditions) may be introduced into the trunk 92 to flare and/or otherwise expand the stent 40. For example, the delivery catheter may be removed, and the distal end 16 of the catheter 12 may be advanced over the same guidewire 98 into the trunk 92. In the embodiment shown in FIG. 1B, a proximal end (not shown) of the guidewire 98 may be backloaded into the opening 34c through the instrument lumen 18c and out the port 32c. The distal end 16 may then be advanced over the guidewire 98 into the patient's body over the guidewire 98.

As shown in FIG. 2C, the distal end 16 may be advanced through the stent 40 and ostium 90 at least partially into the branch 94. For example, the distal end 16 may be positioned such that the inner balloon 22a is positioned within and/or beyond the stent 40, e.g., beyond the first end 42, and the proximal section 27b of the outer balloon 22b is positioned adjacent the ostium 90, e.g., within and/or proximal to the first end 42 of the stent.

Optionally, to facilitate positioning, the catheter 12 may be monitored using fluoroscopy or other external imaging, e.g., to observe and monitor markers 19 (not shown, see FIG. 1B) on the distal end 16. For example, markers 19*a* and 19*b* may be located on the distal end 16 to identify the ends of the substantially uniform main section 25*a* of the inner balloon 22*a*, while proximal marker 19*c* may be located on the distal end 16 to identify the proximal end 24*b* and/or proximal section 27*b* of the outer balloon 22*b*. Thus, with the markers 19, the inner balloon 22*a* may be aligned with the distal end 44 and/or portion of the stent 40 within the branch 94 beyond the ostium 90 and the proximal section 27*b* of the outer balloon 22*b* may be aligned with the first end 42 of the stent 40 and/or the ostium 90, as desired.

Figure 2D:
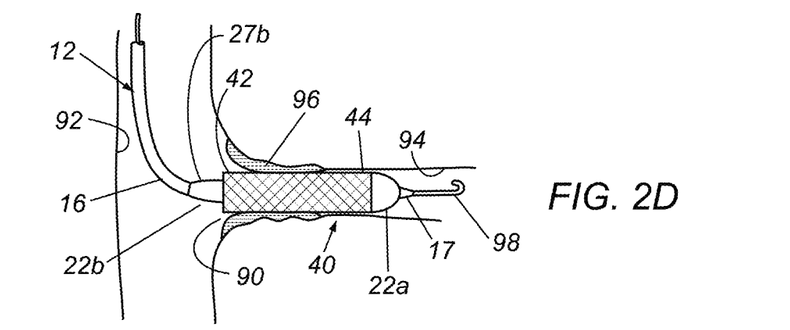

Turning to FIG. 2D, with the catheter 12 positioned as desired, the inner balloon 22*a* may be expanded, e.g., by coupling syringe 11*a* to port 32*a* (not shown in FIG. 2D) and delivering saline, nitrogen, or other inflation media into the interior 23*a* via inflation lumen 18*a*, to engage the stent 40 and/or wall of the branch 94. For example, the inner balloon 22*a* may be expanded to engage both the second end 44 of the stent 40 and the wall of the branch 94 beyond the stent 40 to prevent substantial axial migration of the stent 40.

Figure 2E:
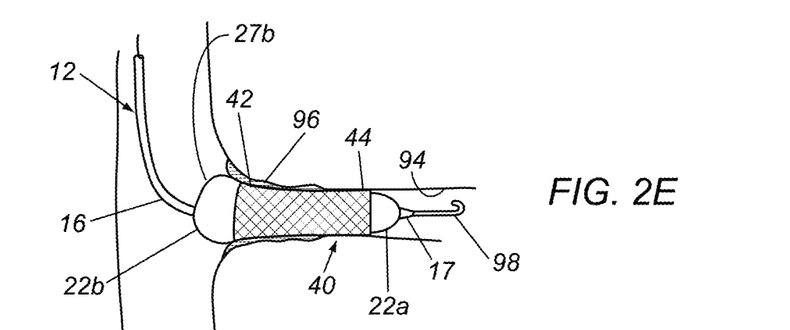

Thereafter, as shown in FIG. 2E, the proximal section 27*b* of the outer balloon 22*b* may be expanded, e.g., by coupling syringe 11*b* to port 32*b* (not shown in FIG. 2E) and delivering saline, nitrogen, or other inflation media into the interior 23*b* via inflation lumen 18*b*, to flare the stent 40. For example, as the proximal section 27*b* is expanded, the first end 42 of the stent 40 is expanded, e.g., into a flared configuration, which may conform to the shape of the proximal section 27*b* and/or the ostium 90.

With the inner balloon 22*a* expanded, the stent 40 and catheter 12 may remain substantially stationary during this inflation and flaring. Otherwise, without the inner balloon 22*a* engaging the stent 40 and wall of the branch 94, there may be a tendency for the stent 40 to migrate distally into the branch 94 rather than flaring in place, e.g., maintaining its substantially uniform diameter, which may shear or otherwise remove material from the lesion 96 and/or wall of the branch 94 and potentially release the material within the branch 94. In addition or alternatively, without the inner balloon 22*a* expanded, there may be a tendency for the distal end 16 of the catheter 12 to move proximally away from the stent 40 and ostium 90. Thus, the inner balloon 22*a* may provide an anchor that ensures the first end 42 of the stent 40 is flared in a desired manner with the stent 40 and catheter 16 substantially fixed relative to one another and the ostium 90.

Figure 2F:
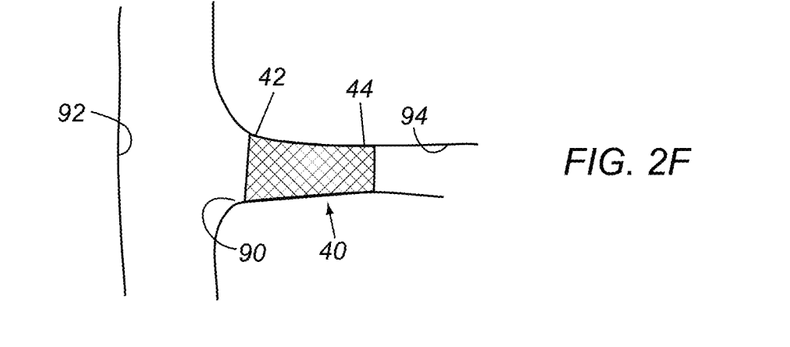

Optionally, after inflating the proximal section 27*b* and flaring the first end 42 of the stent 40, the inner balloon 22*a* may be inflated further, if desired, e.g., to expand the stent 40 and further dilate the lesion 96. With the stent 40 fully deployed, the balloons 22 may be deflated or otherwise collapsed, and the catheter 12 may be withdrawn from the branch 94 and trunk 92, and from the patient's body, e.g., into the guide catheter (not shown). The guide catheter and/or guidewire 98 may then be removed from the patient's body, leaving the stent 40 in place, as shown in FIG. 2F.

In alternative embodiments, other inflation sequences may be used, as desired, e.g., to initially deliver and deploy a stent and then flare the stent, e.g., within an ostium 90. For example, after the stent 40 has been deployed within the branch 94, the distal end 16 may be introduced into the trunk 92. With the proximal section 27*b* within the trunk 92, the outer balloon 22*b* may be partially inflated to expand the proximal section 27*b* before advancing the distal end 16 into the branch 94. When so advanced, the proximal section 27*b* may partially seat within the ostium 90 and/or within the first end 42 of the stent 40. Alternatively, the distal end 16 may be positioned within the branch 94 with the proximal section 27*b* collapsed until the inner and/or outer balloons 22*a*, 22*b* are aligned as desired relative to the ostium 90 and/or stent 40. Once positioned as desired relative to the ostium 90, lesion 96, and/or stent 40, e.g., by observing the markers 19 on the distal end 16, the proximal section 27*b* of the outer balloon 22*b* may be at least partially expanded, e.g., to engage the first end 42 of the stent 40 and/or the ostium 90. During this initial inflation, the first end 42 may be flared or may not be expanded substantially. With the proximal section 27*b* expanded, the distal end 16 may be substantially anchored relative to the stent 40 and branch 94, e.g., to prevent migration of the distal end 16.

The inner balloon 22*a* may then be inflated to expand the stent 40 and/or dilate the lesion 96. During such inflation, there is a tendency for the distal end 16 of the catheter 12 to migrate distally relative to the stent 40 and lesion 96, which may risk causing a dissection distally beyond the stent 40 (what is sometimes called "watermelon seeding"). However, with the proximal section 27*b* expanded to engage the first end 42 of the stent 40 and/or ostium 90, the distal end 16 may be substantially anchored, thereby preventing such migration.

Once the stent 40 is expanded and/or the lesion 96 is dilated by the inner balloon 22*a*, the outer balloon 22*b* may be inflated further, if desired, e.g., to expand the proximal section 27*b* and flare the first end 42 of the stent 40. Thus, the inner and outer balloons 22*a*, 22*b* may be alternately expanded one or more times, as desired, until the stent 40 achieves the desired final configuration.

In another alternative, after initially expanding the proximal section 27*b* of the outer balloon 22*b* within the ostium 90 and/or first end 42 of the stent, the inner balloon 22*a* may be inflated to engage the second end 44 of the stent 40 and the wall of the branch 94 to substantially anchor the stent 40 and catheter 12 relative to one another without necessarily expanding the stent 40 further. The outer balloon 22*b* may then be inflated further to expand the proximal section 27*b* and flare or otherwise shape the first end 42 of the stent 40 relative to the ostium 90. In still another alternative, the apparatus 10 may be used to expand a stent previously placed within a substantially straight or other non-bifurcated body lumen, such as within a carotid, iliac, renal, coronary artery, or other blood vessel. For example, the distal end 16 of the catheter 12 may be introduced into the vessel until the inner balloon 22*a* is aligned with the stent 40. The outer balloon 22*b* may then be inflated such that the proximal section 27*b* engages a first end of the stent and/or the wall of the vessel adjacent the stent 40 to substantially anchor the stent 40, e.g., without dilating the stent 40 and/or vessel. The compliant nature of the outer balloon 22*b* may frictionally engage the vessel wall and/or the stent 40 to prevent substantial migration, e.g., without applying a substantial dilating force. Optionally, at least the proximal section 27*b* of the outer balloon 22*b* may include a surface treatment and/or one or more features that enhance frictional or other engagement with the vessel wall and/or stent 40.

Thereafter, the inner balloon 22*a* may be inflated to expand the stent 40 and/or dilate the lesion or body lumen surrounding the stent 40, as desired, with the outer balloon 22*b* preventing migration of the distal end 16 relative to the stent 40. The balloons 22*a*, 22*b* may then be deflated and the distal end 16 removed from the stent 40 and/or vessel.

In a further alternative, a stent or other prosthesis, such as those disclosed in the applications incorporated by reference herein, may be provided on the distal end 16 of the catheter 12. For example, a stent (not shown) may be delivered directly on the catheter 12, e.g., on one or more both of the balloons 22a, 22b, rather than on a separate delivery catheter, if desired, using similar methods to those described herein and in the applications incorporated by reference herein. Alternatively, a delivery balloon (not shown) may be provided on the distal end 16 of the catheter 12, e.g., proximal or distal to the balloons 22, and a stent may be introduced and deployed on the delivery balloon into an ostial or substantially straight implantation site. The balloons 22a, 22b may then be used to flare and/or expand the stent using similar methods to those described above.

Figure 3A:
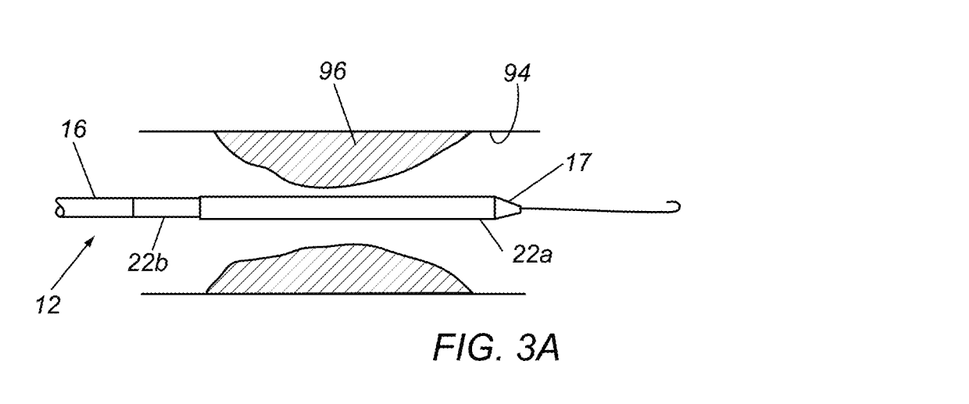
FIGS. 3A-3C are cross-sectional views of a patient's body including a stenosis within a blood vessel, showing a method for dilating the stenosis using the apparatus of FIGS. 1A and 1B.
Figure 3B:
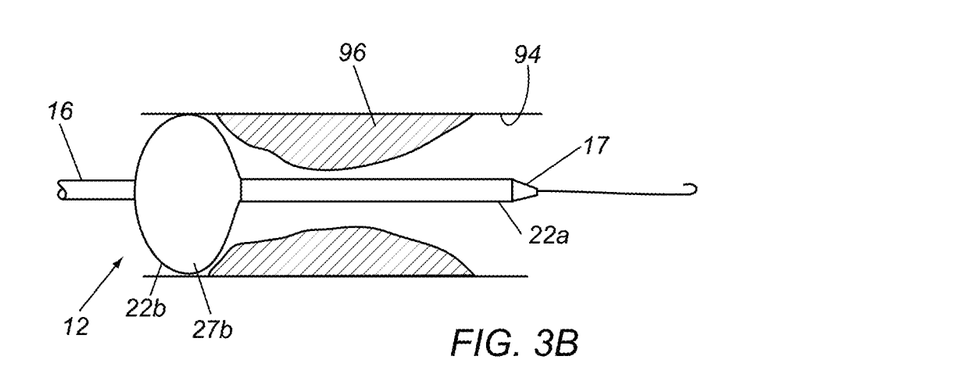
Figure 3C:
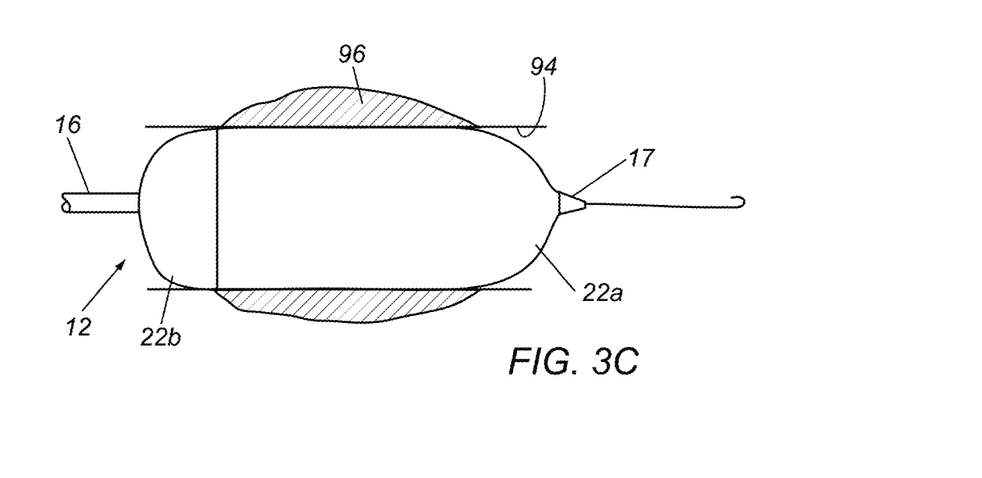

In still another alternative, the apparatus and methods herein may be used to treat a stenosis, occlusion, or other lesion 96 within a body lumen 94 without a stent. For example, as shown in FIGS. 3A-3C, during an angioplasty procedure, after positioning the main section 25a of the inner balloon 22a across a stenosis 96, the proximal section 27b of the outer balloon 22b may be inflated to substantially anchor the distal end 16 relative to the body lumen 94. Alternatively, the outer balloon may be provided distal to the inner balloon or outer balloons may be provided both proximally and distally to the main section 25a of the inner balloon (not shown), as described elsewhere herein.

The inner balloon 22a may then be inflated to expand the main section 25a to dilate the stenosis 96, as desired. In this alternative, the body lumen 94 may be a non-bifurcated body lumen or a body lumen including a branch extending from a trunk. In the latter example (not shown), the distal end 16 may be positioned within the branch, and the outer balloon 22b may be inflated to expand the proximal section 27b to dilate the ostium and/or stenosis therein before or after expanding the main section 25a of the inner balloon 22a within the branch, similar to the methods described elsewhere herein.

In other alternatives, the apparatus and methods herein may be used for treating other structures within a patient's body. For example, the catheter 12 may be used to perform valvuloplasty on heart valves, e.g., an aortic valve of a patient's heart. In this alternative, the main section 25a of the inner balloon 22a may be expandable to diameters of at least nineteen millimeters (19 mm) or more, and the proximal section 27b of the outer balloon 22b may be expandable to larger diameters, e.g., to substantially anchor the distal end 16 of the catheter 12 while the inner balloon 22a is introduced into and expanded to treat the valves, and/or to facilitate additional treatment. For such applications, the inner balloon 22a may be formed from ultra-high pressure materials, such as single resin combinations of balloon materials, such as those described above in combination with PTFE, reinforced fiber composite materials, and/or metallic or polymeric braids, weaves, or other reinforcement structures, e.g., similar to balloons disclosed in U.S. Pat. No. 7,744,620, the entire disclosure of which is expressly incorporated by reference herein.

During use, the inner balloon 22a may be introduced through the site of a natural or prosthetic valve, such as an aortic valve (not shown), and the outer balloon 22b may be expanded to prevent migration and/or otherwise stabilize the distal end 16 relative to the valves. The inner balloon 22a may then be expanded to treat the valve, e.g., to dilate the valve leaflets (not shown) of the valve. In one embodiment, the outer balloon 22b may be located distal to the inner balloon 22a such that the outer balloon 22b is positioned within the left ventricle of the patient's heart, and the inner balloon 22a may extend through the valve annulus, e.g., into the coronary sinus. With the outer balloon 22b expanded within the left ventricle, the outer balloon 22b may contact the heart wall adjacent the aortic valve, thereby preventing the distal end 16 from migrating out of the heart into the aorta. The inner balloon 22a may be expanded one or more times and/or to one or more diameters to dilate the leaflets, e.g., to increase their flexibility and/or separate plaque or other materials on the leaflets.

Optionally, a filter or other embolic protection device (not shown) may be provided on the catheter 10, e.g., proximal to the balloons 22a, 22b, or otherwise introduced into the coronary sinus or aorta of the patient to capture any plaque or other material released during the treatment. For example, an expandable filter (not shown) may be provided on the distal end 16 spaced apart proximally from the balloons 22a, 22b, which may be expanded downstream to the aortic valve before expanding the outer balloon 22b and/or the inner balloon 22a. After the treatment, the filter may be collapsed to capture the released material, e.g., after collapsing the inner balloon 22a and either before or after collapsing the outer balloon 22b. The catheter 10 may be removed from the valve site.

Alternatively, the outer balloon 22b may be provided proximal to the inner balloon 22a. For example, the distal end 16 may be positioned such that the main section of the inner balloon 22a is disposed within the valve annulus, e.g., with the outer balloon 22b located adjacent the leaflets, e.g., within the coronary sinus. The inner balloon 22a may be expanded to initially dilate the leaflets of the valve, and thereafter, if desired, the outer balloon 22b may be expanded to further dilate the leaflets, e.g., direct them outwardly towards or against the wall of the coronary sinus. For example, the inner balloon 22a may be expanded to a first diameter to at least partially dilate the leaflets into the coronary sinus, and then the outer balloon 22b may be expanded to a second larger diameter to further dilate the leaflets. The inner and/or outer balloons 22a, 22b may be expanded and collapsed one or more times, as desired to perform a desired treatment on the valve.

In a further alternative, the outer balloon 22b may be expanded within the coronary sinus or otherwise distal to the valve site before expanding the inner balloon 22a. The outer balloon 22b may contact surrounding tissue to prevent migration of the distal end 16 and/or to prevent plaque or other released material from traveling downstream. Optionally, a filter or other embolic protection device may be deployed proximal to the outer balloon 22b, if desired, as described above. The inner balloon 22a may then be expanded one or more times to treat the leaflets, as described above, and then the balloons 22a, 22b may be collapsed and the catheter 10 removed from the valve site. Optionally, in this alternative, the catheter 10 may include an aspiration port adjacent the balloons 22a, 22b for aspirating released material captured by the outer balloon 22b.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for flaring a stent previously deployed within a branch body lumen including an ostium communicating with a main body lumen, a first end of the stent extending at least partially from the branch body lumen into the ostium, the method comprising:
 providing an elongate member including a proximal end, a distal end, an expandable member carried on the distal end that includes a substantially uniform diameter distal section, and a proximal section extending proximally from the distal section, wherein at least the proximal section comprises compliant material molded to a shape in which the proximal section has a bulbous shape defining a first diameter and wherein the distal section has a substantially cylindrical shape defining a second diameter smaller than the first diameter;
 introducing the distal end into the main body lumen;
 positioning the distal end of the elongate member through the ostium and stent into the branch body lumen until the distal section is disposed within the stent;
 initially expanding the expandable member to engage the distal section within the stent to substantially anchor the stent axially relative to the branch body lumen; and
 expanding the proximal section to flare the first end of the stent within the ostium.

2. The method of claim 1, further comprising, after expanding the proximal section, further expanding the expandable member to expand the stent within the branch body lumen.

3. The method of claim 2, wherein the diameter of the branch body lumen does not increase substantially when the expandable member is initially expanded to engage the distal section within the stent, and wherein the branch body lumen is dilated when the expandable member is further expanded to expand the stent.

4. The method of claim 1, wherein positioning the distal end of the elongate member comprises positioning the distal end of the elongate member such that the proximal section is disposed adjacent the ostium before initially expanding the expandable member.

5. The method of claim 4, further comprising monitoring markers on the distal end of the elongate member to facilitate positioning the proximal section adjacent the ostium.

6. The method of claim 1, wherein initially expanding the expandable member prevents the stent from migrating substantially when the proximal section is expanded.

7. The method of claim 1, wherein the material of the expandable member has a thinner wall thickness along the proximal section than along the distal section.

8. The method of claim 1, further comprising delivering energy from one or more elements on the expandable member to surrounding tissue adjacent the stent.

9. A method for treating a lesion within a branch body lumen including an ostium communicating with a main body lumen, the method comprising:
 introducing a distal end of a delivery catheter into the main body lumen, the delivery catheter distal end carrying a stent in a contracted condition;
 positioning the delivery catheter distal end within the branch body lumen such that a first end of the stent is disposed adjacent the ostium and a second end of the stent is disposed further within the branch body lumen;
 expanding the stent such that the stent engages surrounding tissue of the branch body lumen;
 removing the delivery catheter from the branch body lumen and main body lumen;
 introducing a distal end of a flaring catheter into the main body lumen, the flaring catheter comprising a proximal end, a distal end, an expandable member carried on the flaring catheter distal end that includes a substantially uniform diameter distal section when expanded, and a proximal section extending proximally from the distal section; wherein at least the proximal portion comprises compliant material molded to a shape in which the proximal section has a bulbous shape defining a first diameter and the distal section has a substantially cylindrical shape defining a second diameter smaller than the first diameter;
 positioning the flaring catheter distal end through the ostium and stent into the branch body lumen until the distal section is disposed within the stent;
 initially expanding the distal section to substantially anchor the stent axially relative to the branch body lumen; and
 thereafter, continuing expanding the proximal section to flare the first end of the stent within the ostium.

10. The method of claim 9, wherein the lesion is dilated when the stent is initially expanded on the delivery catheter to a substantially uniform diameter.

11. The method of claim 10, further comprising, after expanding the proximal section, further expanding the expandable member to expand the distal section to expand the stent further within the branch body lumen and dilate the lesion further.

12. The method of claim 9, further comprising, after expanding the proximal section, further expanding the expandable member to expand the stent within the branch body lumen.

13. The method of claim 12, wherein the diameter of the branch body lumen does not change when the expandable member is initially expanded, and wherein the branch body lumen is dilated when the expandable member is further expanded to expand the stent.

14. The method of claim 9, further comprising introducing a distal end of a guidewire into the main body lumen and through the ostium into the branch body lumen, and wherein the delivery catheter distal end is introduced into the main body lumen and positioned within the branch body lumen over the guidewire.

15. The method of claim 14, wherein the flaring catheter distal end is introduced into the main body lumen over the guidewire after removing the delivery catheter.

16. The method of claim 9, wherein positioning the distal end of the flaring catheter comprises positioning the flaring catheter distal end such that the proximal section is disposed adjacent the ostium before initially expanding the expandable member.

17. The method of claim 16, further comprising monitoring markers on the flaring catheter distal end to facilitate positioning the proximal section adjacent the ostium.

18. The method of claim 9, wherein initially expanding the expandable member prevents the stent from migrating substantially when the proximal section is expanded.

19. The method of claim 9, further comprising delivering energy from one or more elements on the expandable member to surrounding tissue adjacent the stent.

* * * * *